United States Patent [19]

Kuroda et al.

[11] Patent Number: 5,208,371

[45] Date of Patent: May 4, 1993

[54] PROCESS FOR PRODUCTION OF METHACROLEIN AND METHACRYLIC ACID

[75] Inventors: Tooru Kuroda; Motomu Oh-Kita; Masaaki Kato, all of Hiroshima, Japan

[73] Assignee: Mitsubishi Rayon Co., Ltd., Tokyo, Japan

[21] Appl. No.: 873,223

[22] Filed: Apr. 24, 1992

Related U.S. Application Data

[63] Continuation of Ser. No. 761,313, Sep. 17, 1991, abandoned, which is a continuation of Ser. No. 114,589, Oct. 30, 1987, abandoned.

[30] Foreign Application Priority Data

Nov. 11, 1986 [JP] Japan .................. 61-266550

[51] Int. Cl.$^5$ .................... C07C 51/16; B01J 21/08
[52] U.S. Cl. .................... 562/538; 562/544; 502/228; 502/242
[58] Field of Search ............ 502/228, 242, 243, 248; 562/538, 544

[56] References Cited

U.S. PATENT DOCUMENTS

| | | | |
|---|---|---|---|
| 3,954,856 | 5/1976 | Kobayashi et al. | 260/533 |
| 3,972,920 | 8/1976 | Ishii et al. | 260/533 |
| 4,035,418 | 7/1977 | Okada et al. | 252/531 |
| 4,111,984 | 9/1978 | Ishii et al. | 260/533 |
| 4,111,985 | 9/1978 | Okada et al. | 260/533 |
| 4,219,670 | 8/1980 | Okada et al. | 260/533 |
| 4,259,211 | 5/1981 | Krabetz et al. | 252/443 |
| 4,374,759 | 2/1983 | Khooblar | 252/455 R |
| 4,380,664 | 4/1983 | Ishii et al. | 562/546 |
| 4,511,671 | 4/1985 | Saito et al. | 502/242 |
| 4,537,874 | 8/1985 | Sato et al. | 502/311 |
| 4,556,731 | 12/1985 | Guttman | 562/546 |

FOREIGN PATENT DOCUMENTS

0102641 3/1984 European Pat. Off. .
2354812 1/1978 France .
2435456 4/1980 France .
61-22040 1/1986 Japan .

OTHER PUBLICATIONS

Patents abstracts of Japan, vol. 10, No. 172 (C-354) [2228], Jun. 18, 1986.
The Selective Oxidation of Olefins Multicomponent Molybdate Catalysts, Thesis (1974) at pp. 25-30.
Shimizu et al., Development of Catalyst for Production of Methacrylic Acids (1988).

*Primary Examiner*—Arthur C. Prescott
*Attorney, Agent, or Firm*—Cushman, Darby & Cushman

[57] ABSTRACT

The invention provides a process for industrially and advantageous production of methacrolein and methacrylic acid which comprises subjecting isobutylene or tert-butanol to gas phase catalytic oxidation with a molecular oxygen-containing gas in the presence of a catalyst having the composition represented by the following formula:

$$Mo_aW_bBi_cFe_dSb_eCr_fSi_gA_hX_iY_jZ_kO_l$$

wherein Mo, W, B, Fe, Sb, Cr, Si and O represent molybdenum, tungsten, bismuth, iron, antimony, chromium, silicon and oxygen, respectively; A represents at least one element selected from the group consisting of nickel and cobalt; X represents at least one element selected from the group consisting of potassium, rubidium, cesium and thallium; Y represents at least one element selected from the group consisting of magnesium, zinc, manganese, cadmium, lead and barium; Z represents at least one element selected from the group consisting of phosphorus, boron, sulfur, chlorine, cerium, tin and titanium; a, b, c, d, e, f, g, h, i, j, k and l each represents atomic ratio of each element; and when a is 12, b is 0.01-2, c is 0.01-3, d is 0.5-4, e is 0.01-3, f is 0.01-3, g is 1-20, h is 1-12, i is 0.01-2, j is 0.01-5 and k is 0-3 and l is the number of oxygen atom necessary to satisfy valence of each of said component.

4 Claims, No Drawings

PROCESS FOR PRODUCTION OF METHACROLEIN AND METHACRYLIC ACID

RELATED APPLICATIONS

This application is a continuation of application Ser. No. 07/761,313 filed Sep. 17, 1991 now abandoned which was a continuation of application Ser. No. 07/114,589 filed Oct. 30, 1987 now abandoned.

BACKGROUND OF THE INVENTION

This invention relates to a process for production of methacrolein and methacrylic acid by gas phase catalytic oxidation of isobutylene or tertbutanol with molecular oxygen.

Many proposals have been made for catalysts used in production of methacrolein and methacrylic acid by gas phase catalytic oxidation of isobutylene or tert-butanol at high temperatures. However, from an industrial viewpoint, the catalysts used in this reaction have been demanded to be improved in catalytic efficiencies such as catalytic activity, selectivity for methacrolein and methacrylic acid, life of catalyst, etc.

U.S. Pat. No. 4,537,874 discloses MoWBiFe (Ni, Co) alkali metal catalysts, but makes no mention of Cr. Besides, the main feature of the patent resides in subjecting Bi compound and W compound to previous calcination treatment at 600°–900° C. and preparation of catalysts is complicated.

SUMMARY OF THE INVENTION

This invention is a process for producing methacrolein and methacrylic acid, characterized by gas phase catalytic oxidation of isobutylene or tert-butanol with a molecular oxygen-containing gas in the presence of a catalyst having a composition represented by the following formula:

$$Mo_aW_bBi_cFe_dSb_eCr_fSi_gA_hX_iY_jZ_kO_l$$

wherein Mo, W, Bi, Fe, Sb, Cr, Si and O represent molybdenum, tungsten, bismuth, iron, antimony, chromium, silicon and oxygen, respectively, A represents at least one element selected from the group consisting of nickel and cobalt; X represents at least one element selected from the group consisting of potassium, rubidium, cesium and thallium; Y represents at least one element selected from the group consisting of magnesium, zinc, manganese, cadmium, lead and barium; Z represents at least one element selected from the group consisting of phosphorus, boron, sulfur, chlorine, cerium, tin and titanium; and a, b, c, d, e, f, g, h, i, j, k and l each represents atomic ratio of each element. When $a=12$, $b=0.01-2$, preferably 0.03–1; $c=0.01-3$, preferably 0.1–2; $d=0.5-4$, preferably 1–3.5; $e=0.01-3$, preferably 0.1–2; $f=0.01-3$, preferably 0.03–1; $g=1-20$, preferably 3–18; $h=1-12$, preferably 3–10; $i=0.01-2$, preferably 0.05–1; $j=0.01-5$, preferably 0.1–4; and $k=0-3$, preferably 0–1; and l is the number of oxygen atom necessary to satisfy the valency of each of said component.

DESCRIPTION OF THE INVENTION

As starting materials for said elements in preparation of catalysts used in this invention, there may be preferably used oxides or chlorides, sulfates, nitrates or carbonates which are able to convert to oxides upon strong heating or mixtures thereof. Preparation of catalysts is effected by known methods such as evaporation to dryness, precipitation, mixing of oxides, etc. The catalyst component supported on a carrier may be used. The carrier includes, for example, silica, alumina, silica-alumina, etc.

In practice of this invention, a molecular oxygen-containing gas is added to the starting isobutylene or tert-butanol and gas phase catalytic oxidation thereof is effected in the presence of said catalyst. Molar ratio of isobutylene or tert-butanol: oxygen is preferably 1:0.5–3. The feed gas is preferably diluted with an inert gas. The molecular oxygen used for oxidation may be either pure oxygen gas or air, but industrially air is advantageous. Reaction pressure may be from atmospheric pressure to several atms. Reaction temperature is preferably 250°–450° C. The reaction may be performed by fluidized bed or fixed bed.

According to the process of this invention, methacrolein and methacrylic acid are industrially and advantageously obtained from isobutylene or tert-butanol. Further, according to this invention, catalysts which are able to produce industrially and advantageously methacrolein and methacrylic acid from isobutylene or tert-butanol are obtained without subjecting Bi compound and W compound to high temperature calcination treatment. Thus, preparation of catalyst is easy.

All "part" in the following examples mean "part by weight" and analysis was carried out by gas chromatography. The conversion of isobutylene or tert-butanol, the selectivities for methacrolein and methacrylic acid produced and per-pass yield are defined as follows:

Conversion (%) of isobutylene or tert-butanol =

$$\frac{\text{Mol number of altered isobutylene or tert-butanol}}{\text{Mol number of fed isobutylene or tert-butanol}} \times 100$$

Selectivity (%) for methacrolein =

$$\frac{\text{Mol number of produced methacrolein}}{\text{Mol number of altered isobutylene or tert-butanol}} \times 100$$

Selectivity (%) for methacrylic acid =

$$\frac{\text{Mol number of produced methacrylic acid}}{\text{Mol number of altered isobutylene or tert-butanol}} \times 100$$

Per-pass yield (%) of (methacrolein + methacrylic acid) =

$$\frac{\text{Mol number of produced (methacrolein + methacrylic acid)}}{\text{Mol number of fed isobutylene or tert-butanol}} \times 100$$

EXAMPLE 1

To 1000 parts of water were added 500 parts of ammonium molybdate, 18.5 parts of ammonium paratungstate, 18.4 parts of cesium nitrate and 354.5 parts of 20% silica sol, followed by stirring under heating. (Solution A).

Separately, 250 parts of 60% nitric acid was added to 850 parts of water to obtain homogeneous solution. Then, 57.2 parts of bismuth nitrate was added thereto to dissolve it. To the solution were added successively 238.4 parts of ferric nitrate, 4.7 parts of chromium nitrate, 411.8 parts of nickel nitrate and 60.5 parts of magnesium nitrate to dissolve them. (Solution B).

Solution B was added to Solution A to make a slurry and thereto was added 34.4 parts of antimony trioxide, followed by stirring under heating to evaporate most of water.

The resulting cake-like substance was dried at 120° C. and then calcined at 500° C. for 6 hours and subjected to pressure molding.

The obtained catalyst had the following composition:

$Mo_{12}W_{0.3}Bi_{0.5}Fe_{2.5}Sb_1Cr_{0.05}Si_5Ni_6Cs_{0.4}Mg_1O_l$.

The atomic ratio l of oxygen is automatically determined depending on valences of other elements and so will be omitted hereinafter.

This catalyst was charged in a stainless steel reaction tube and a mixed feed gas comprising 5% of isobutylene, 12% of oxygen, 10% of water vapor and 73% of nitrogen was allowed to pass through the catalyst layer for a contact time of 3.6 seconds and reaction was carried out at 360° C. The results were as follows: conversion of isobutylene: 96%; selectivity for methacrolein: 86.7%; selectivity for methacrylic acid: 5.0%; and per-pass yield of (methacrolein+methacrylic acid): 88.0%.

EXAMPLES 2-9

The following catalysts were prepared according to the procedure of Example 1.

Example 2: $Mo_{12}W_{0.5}Bi_{0.3}Fe_{1.5}Sb_{0.8}Cr_{0.05}Si_7Co_7K_{0.3}Zn_1$

Example 3: $Mo_{12}W_{0.3}Bi_1Fe_3Sb_1Cr_{0.1}Si_{10}Ni_4Co_3Rb_{0.5}Mn_{0.5}P_{0.08}$ Example 4: $Mo_{12}W_{0.1}Bi_1Fe_3Sb_1Cr_{0.1}Si_{10}Ni_4Co_3K_{0.2}Cs0.3Cd_{0.5}B_{0.3}$.

Example 5: $Mo_{12}W_{0.1}Bi_1Fe_3Sb_1Cr_{0.1}Si_{12}Ni_4Co_3Tl_{0.2}Pb_{0.1}S_{0.8}$ Example 6: $Mo_{12}W_{0.3}Bi_1Fe_3Sb_1Cr_{0.3}Si_{15}Ni_4Co_3Tl_{0.2}Ba_{0.3}Cl_{0.5}$ Example 7: $Mo_{12}W_{0.3}Bi_1Fe_3Sb_1Cr_{0.3}Si_7Ni_4Co_3Tl_{0.2}Mg_{1.5}Zn_{0.5}Ce_{0.5}$ Example 8: $Mo_{12}W_{0.3}Bi_1Fe_3Sb_1Cr_{0.3}Si_{10}Ni_6Tl_{0.2}Mg_{1.5}Sn_{0.5}Ti_{0.5}$ Example 9: $Mo_{12}W_{0.3}Bi_1Fe_3Sb_1Cr_{0.1}Si_{10}Co_6Cs_{0.2}Tl_{0.1}Mg_{0.5}Zn_{1.5}$ Reactions were carried out using these catalysts in the same manner as in Example 1 with changing reaction temperature. The results are shown in Table 1.

EXAMPLES 10-12

Reactions were carried out using the catalysts of Examples 1-3 in the same manner as in Example 1 except that tert-butanol was used as the starting material. The results are shown in Table 2.

TABLE 2

| | Reaction temperature (°C.) | Convertion of tert-butanol (%) | Selectivity for methacrolein (%) | Selectivity for methacrylic acid (%) | Per-pass yield of (methacrolein + methacrylic acid) (%) |
|---|---|---|---|---|---|
| Example 10 | 360 | 100 | 86.0 | 3.3 | 89.3 |
| Example 11 | 360 | 100 | 85.8 | 3.4 | 89.2 |
| Example 12 | 360 | 100 | 85.7 | 3.3 | 89.0 |

COMPARATIVE EXAMPLE 1

A catalyst having the following composition was prepared in the same manner as in Example 1 except that 354.5 parts of 20% silica sol, 4.7 parts of chromium nitrate and 60.5 parts of magnesium nitrate were omitted.

$Mo_{12}W_{0.3}Bi_{0.5}Fe_{2.5}Sb_1Ni_6Cs_{0.4}$.

Reaction was carried out using this catalyst in the same manner as in Example 1. The results were as follows: the conversion of isobutylene: 90%; the selectivity for methacrolein: 85.0%; the selectivity for methacrylic acid: 4.3%; and per-pass yield of (methacrolein+methacrylic acid): 80.4%.

COMPARATIVE EXAMPLE 2

Reaction was effected using the catalyst of Comparative Example 1 in the same manner as in Example 10. The results were as follows: the conversion of tert-butanol: 100%; the selectivity for methacrolein: 78.0%; the selectivity for methacrylic acid: 3.4%; and per-pass yield of (methacrolein+methacrylic acid): 81.4%.

COMPARATIVE EXAMPLE 3

A catalyst having the following composition was prepared in the same manner as in Example 1 except that 354.5 parts of 20% silica sol and 4.7 parts of chromium nitrate were omitted.

$Mo_{12}W_{0.3}Bi_{0.5}Fe_{2.5}Sb_1Ni_6Cs_{0.4}Mg_1$.

Reaction was carried out using this catalyst in the same manner as in Example 1. The results were as follows: the conversion of isobutylene: 95%; the selectivity for methacrolein: 86.0%; the selectivity for meth-

TABLE 1

| | Reaction temperature (°C.) | Convertion of isobutylene (%) | Selectivity for methacrolein (%) | Selectivity for methacrylic acid (%) | Per-pass yield of (methacrolein + methacrylic acid) (%) |
|---|---|---|---|---|---|
| Example 2 | 360 | 97 | 87.0 | 3.6 | 87.9 |
| Example 3 | 360 | 95 | 87.9 | 4.5 | 87.8 |
| Example 4 | 365 | 95 | 87.0 | 5.3 | 87.7 |
| Example 5 | 365 | 93 | 91.0 | 3.6 | 88.0 |
| Example 6 | 365 | 94 | 90.0 | 3.7 | 88.1 |
| Example 7 | 360 | 96 | 88.5 | 3.5 | 88.3 |
| Example 8 | 365 | 94 | 88.0 | 5.6 | 88.0 |
| Example 9 | 360 | 96 | 89.0 | 3.0 | 88.3 | acrylic acid: 4.8%; and per-pass yield of (methacrolein+methacrylic acid): 86.3%.

COMPARATIVE EXAMPLE 4

Reaction was carried out using the catalyst of Comparative Example 3 in the same manner as in Example 10. The results were as follows: the conversion of tert-butanol: 100%; the selectivity for methacrolein; 84.5%; the selectivity for methacrylic acid: 3.0%; and per-pass yield of (methacrolein+methacrylic acid): 87.5%.

COMPARATIVE EXAMPLE 5

A catalyst having the following composition was prepared in the same manner as in Example 1 except that 4.7 parts of chromium nitrate was omitted.

$$Mo_{12}W_{0.3}Bi_{0.5}Fe_{2.5}Sb_1Si_5Ni_6Cs_{0.4}Mg_1$$

Reaction was carried out using this catalyst in the same manner as in Example 1. The results were as follows: the conversion of isobutylene: 96%; the selectivity for methacrolein: 85.3%, the selectivity for methacrylic acid: 5.0%; and per-pass yield of (methacrolein+methacrylic acid): 86.7%.

COMPARATIVE EXAMPLE 6

Reaction was carried out using the catalyst of Comparative Example 5 in the same manner as in Example 10. The results were as follows: the conversion of tert-butanol: 100%; the selectivity for methacrolein: 84.4%; the selectivity for methacrylic acid: 3.3%; and per-pass yield of (methacrolein+methacrylic acid): 87.7%.

COMPARATIVE EXAMPLE 7

A catalyst having the following composition was prepared in the same manner as in Example 1 except that 18.5 parts of ammonium paratungstate, 354.5 parts of 20% silica sol and 4.7 parts of chromium nitrate were omitted.

$$Mo_{12}Bi_{0.5}Fe_{2.5}Sb_1Ni_6Cs_{0.4}Mg_1$$

Reaction was carried out using this catalyst in the same manner as in Example 1. The results were as follows: the conversion of isobutylene: 90%; the selectivity for methacrolein: 86.8%, the selectivity for methacrylic acid: 5.2%; and per-pass yield of (methacrolein+methacrylic acid): 82.8%.

COMPARATIVE EXAMPLE 8

Reaction was carried out using the catalyst of Comparative Example 7 in the same manner as in Example 10 to obtain the following results: the conversion of tert-butanol: 100%; the selectivity for methacrolein: 80.0%; the selectivity for methacrylic acid: 3.3%, and per-pass yield of (methacrolein+methacrylic acid): 83.3%.

We claim:

1. A process for producing methacrolein and methacrylic acid which comprises subjecting isobutylene or tert-butanol to gas phase catalytic oxidation with a molecular oxygen-containing gas in the presence of a catalyst having the composition represented by the following formula:

$$Mo_aW_bBi_cFe_dSb_eCr_fSi_gA_hX_iY_jZ_kO_l$$

wherein Mo, W, Bi, Fe, Sb, Cr, Si and O represent molybdenum, tungsten, bismuth, iron, antimony, chromium, silicon and oxygen, respectively; A represents at least one element selected from the group consisting of nickel and cobalt; X represents at least one element selected from the group consisting of potassium, rubidium, cesium and thallium; Y represents at least one element selected from the group consisting of magnesium, zinc, manganese, cadmium, lead and barium; Z represents at least one element selected from the group consisting of phosphorus, boron, sulfur, chlorine, cerium, tin and titanium; a, b, c, d, e, f, f, g, h, i, j, k and l each represents the atomic ratio of each element; and wherein a is 12, b is 0.03–1, c is 0.1–2, d is 1–3.5, e is 0.1–2, f is 0.03–1, g is 3–18, h is 3–10, i is 0.05–1, j is 0.1–4 and k is 0–1 and l is the number of oxygen atom necessary to satisfy valence of each of said component.

2. A process according to claim 1 wherein the starting material is isobutylene.

3. A process according to claim 1 wherein the starting material is tert-butanol.

4. A process according to claim 1, wherein, in the formula, $0 < k \leq 1$.

* * * * *